US011821014B2

United States Patent
Anderson et al.

(10) Patent No.: US 11,821,014 B2
(45) Date of Patent: Nov. 21, 2023

(54) PRODUCTION OF GENTISIC ACID 5-O-β-D XYLOPYRANOSIDE

(71) Applicant: Frito-Lay North America, Inc., Plano, TX (US)

(72) Inventors: Nickolas Anderson, Arden Hills, MN (US); Amanda Waters, Champlin, MN (US)

(73) Assignee: Frito-Lay North America, Inc., Plano, TX (US)

(*) Notice: Subject to any disclaimer, the term of this patent is extended or adjusted under 35 U.S.C. 154(b) by 299 days.

(21) Appl. No.: 17/122,027

(22) Filed: Dec. 15, 2020

(65) Prior Publication Data

US 2022/0186275 A1  Jun. 16, 2022

(51) Int. Cl.
*C12N 15/82* (2006.01)
*C12P 19/44* (2006.01)
*C12N 9/10* (2006.01)
*C12P 19/18* (2006.01)

(52) U.S. Cl.
CPC ............ *C12P 19/44* (2013.01); *C12N 9/1077* (2013.01); *C12N 15/8245* (2013.01); *C12P 19/18* (2013.01)

(58) Field of Classification Search
CPC ...... C07K 14/415; C12N 15/81; C12N 15/70; C12N 15/8245; C12N 9/1048; C12N 15/8281
See application file for complete search history.

(56) References Cited

U.S. PATENT DOCUMENTS

2016/0215306 A1* 7/2016 Baerends ............. C12N 9/1051
2018/0346921 A1  12/2018 Rayment et al.

FOREIGN PATENT DOCUMENTS

| EP | 1649029 B1 | 12/2014 |
| WO | 02/088346 | 11/2002 |
| WO | 03/078614 | 9/2003 |
| WO | 03/078637 | 9/2003 |
| WO | 2015/028324 | 3/2015 |

OTHER PUBLICATIONS

Tárraga, Susana, et al. "Molecular cloning and characterization of a novel tomato xylosyltransferase specific for gentisic acid." Journal of experimental botany 61.15 (2010): 4325-4338. (Year: 2010).*
Pham, Gina M., et al. "Construction of a chromosome-scale long-read reference genome assembly for potato." Gigascience 9.9 (2020): giaa100. (Year: 2020).*
Kubo, Akiko, et al. "Alteration of sugar donor specificities of plant glycosyltransferases by a single point mutation." Archives of Biochemistry and Biophysics 429.2 (2004): 198-203. (Year: 2004).*
Tarraga et al., "Molecular cloning and characterization of a novel tomato xylosyltransferase specific for gentisic acid," Journal of Experimental Botany, vol. 61, No. 15, pp. 4325-4338, 2010.
Skerker, "Dissecting a Complex Chemical Stress: Chemogenomic Profiling of Plant Hydrolysates," Molecular Systems Biology 9; Article No. 674, 2013.
Rosenberger et al., "UDP-Xylose and UDP-galactose Synthesis in Trichomonas Vaginalis," Mol Biochem Parasitol, 181 (1-2): 53-56, Jan. 2012.
Chen et al., "Identification of a Residue Responsible for UDP-sugar Donor Selectivity of a Dihydroxybenzoic Acid Glycosyltransferase from Arabidopsis Natural Accessions," The Plant Journal (2017) 89, 195-203.
Härtl K., McGraphery K., Rüdiger J., Schwab W. (2018) Tailoring Natural Products with Glycosyltransferases. In: Schwab W., Lange B., Wüst M. (eds) Biotechnology of Natural Products. Springer, Cham. https://doi.org/10.1007/978-3-319-67903-7_9.
Fayos et al., "Induction of Gentisic Acid 5-o-@b-d-xylopyranoside in Tomato and Cucumber Plants Infected by Different Pathogens," Phytochemistry, Elsevier, Amsterdam, NL, vol. 67, No. 2, Jan. 1, 2006.
Taniguchi N et al., "A Glycomic Approach to the Identification and Characterization of Glycoprotein Function in Cells Transfected with Glycosyltransferase Genes," Proteomics, Wiley-VCH Verlag, Weinheim, DE, vol. 1, Jan. 20, 2001.
International Search Report and Written Opinion dated Mar. 18, 2022 in PCT/US2021/063610.

* cited by examiner

Primary Examiner — Weihua Fan
(74) Attorney, Agent, or Firm — Barnes & Thornburg LLP; Aisha R. Hasan

(57) ABSTRACT

An expression vector that includes a polynucleotide having a heterologous regulatory element operably linked to a polynucleotide sequence derived from *Solanum tuberosum* and encoding a xylosyltransferase capable of glycosylating gentisic acid to produce gentisic acid 5-O-β-D xylopyranoside, a transcription template having such a polynucleotide and adapted for in vitro transcription in a cell-free system, a method for producing gentisic acid 5-O-β-D xylopyranoside by culturing a recombinant host cell containing such an expression vector under conditions in which the cell expresses the xylosyltransferase from the polynucleotide, and a method for producing gentisic acid 5-O-β-D xylopyranoside by contacting a composition including gentisic acid and UDP-xylose with a recombinant xylosyltransferase. The recombinant host cell containing such an expression vector can be a bacterial cell, a plant cell, or a fungal cell, an animal cell, or a multicellular organism such as a plant.

13 Claims, No Drawings
Specification includes a Sequence Listing.

SEQUENCE LISTING

<160> NUMBER OF SEQ ID NOS: 2

<210> SEQ ID NO 1
<211> LENGTH: 1794
<212> TYPE: DNA
<213> ORGANISM: Solanum tuberosum
<220> FEATURE:
<221> NAME/KEY: exon
<222> LOCATION: (217)..(1609)

<400> SEQUENCE: 1

```
atcgactaac tataagaacc acaagatttt cccatccata aattgtcatt ccttcaattg      60
agaagttgca taagatttta agaagaacga aaacgatttc tacatcgtac ttactagggt     120
tgatttctca gataattatt tagcttaagt tgatcataaa gcatctttct tcttgattga     180
tttttccttc agccattaat tgagaagtag caagag atg act act cac cag gct      234
                                       Met Thr Thr His Gln Ala
                                         1               5 cac tgt ttg att ttg tca tat cca gtc caa ggt cat atc aac cca atg      282
His Cys Leu Ile Leu Ser Tyr Pro Val Gln Gly His Ile Asn Pro Met
         10                  15                  20 ctc caa ttc tcc aaa cgt tta caa tcc aaa cgt gtt aaa atc act ata      330
Leu Gln Phe Ser Lys Arg Leu Gln Ser Lys Arg Val Lys Ile Thr Ile
     25                  30                  35 gca ctc aca aaa tcc ttt ttg aaa aac atg aaa gaa ttg cca act tct      378
Ala Leu Thr Lys Ser Phe Leu Lys Asn Met Lys Glu Leu Pro Thr Ser
 40                  45                  50 atg tca atc gag gcc ata tct gat ggc tat gat gat ggt ggt cgc gat      426
Met Ser Ile Glu Ala Ile Ser Asp Gly Tyr Asp Asp Gly Gly Arg Asp
 55                  60                  65                  70 caa gca gga tct ttc gtt gcc tat gtt aca cga ttc aaa gaa gtt ggc      474
Gln Ala Gly Ser Phe Val Ala Tyr Val Thr Arg Phe Lys Glu Val Gly
                 75                  80                  85 tcg gat act ctt tct caa ctt att caa aaa ttg gca aat agt gga tgc      522
Ser Asp Thr Leu Ser Gln Leu Ile Gln Lys Leu Ala Asn Ser Gly Cys
         90                  95                 100 cct gta aat tgc ata gta tat gat cca ttc ctc cct tgg gct gtt gaa      570
Pro Val Asn Cys Ile Val Tyr Asp Pro Phe Leu Pro Trp Ala Val Glu
        105                 110                 115 gtt gca aag aat ttt gga tta att agt gct gca ttt ttc aca caa aat      618
Val Ala Lys Asn Phe Gly Leu Ile Ser Ala Ala Phe Phe Thr Gln Asn
    120                 125                 130 tgt gct gtg gat aac att tat tac cat gta cat aaa ggg gta ata aaa      666
Cys Ala Val Asp Asn Ile Tyr Tyr His Val His Lys Gly Val Ile Lys
135                 140                 145                 150 ctt cca cct act caa aat aat gaa gaa ata tta att cct gga ttt tca      714
Leu Pro Pro Thr Gln Asn Asn Glu Glu Ile Leu Ile Pro Gly Phe Ser
                155                 160                 165 agt cca att gag gca tca gat gca cct act ttt gtt att gat cct gaa      762
Ser Pro Ile Glu Ala Ser Asp Ala Pro Thr Phe Val Ile Asp Pro Glu
            170                 175                 180 gca gaa aga ata ctt gaa atg ttg gtc aat caa ttc tca aat ctt gac      810
Ala Glu Arg Ile Leu Glu Met Leu Val Asn Gln Phe Ser Asn Leu Asp
        185                 190                 195 aaa gtg gat tgg gtc cta atc aat agt ttc tat gag ttg gaa aaa gag      858
Lys Val Asp Trp Val Leu Ile Asn Ser Phe Tyr Glu Leu Glu Lys Glu
    200                 205                 210 gta att gat tgg atg tcc aag atg tat cca atc aag aca att gga cca      906
Val Ile Asp Trp Met Ser Lys Met Tyr Pro Ile Lys Thr Ile Gly Pro
215                 220                 225                 230
```

| | |
|---|---|
| aca ata cca tca atg tac tta gac aag aga cta cat gat gac aaa gag<br>Thr Ile Pro Ser Met Tyr Leu Asp Lys Arg Leu His Asp Asp Lys Glu<br>                       235                       240                       245 | 954 |
| tat ggc ctt agt atc ttc aag cca atg aca aat gaa tgc cta aat tgg<br>Tyr Gly Leu Ser Ile Phe Lys Pro Met Thr Asn Glu Cys Leu Asn Trp<br>                       250                       255                       260 | 1002 |
| tta aat cat caa cca att agc tca gtg gtg tat gta tca ttt gga agt<br>Leu Asn His Gln Pro Ile Ser Ser Val Val Tyr Val Ser Phe Gly Ser<br>                       265                       270                       275 | 1050 |
| tta gcc aaa tta gaa gct gag caa atg gaa gaa ttg gca tgt ggt ttg<br>Leu Ala Lys Leu Glu Ala Glu Gln Met Glu Glu Leu Ala Cys Gly Leu<br>                       280                       285                       290 | 1098 |
| agg aat agc aat aaa aac ttc ttg tgg gtt gtt agg tcc att gaa gaa<br>Arg Asn Ser Asn Lys Asn Phe Leu Trp Val Val Arg Ser Ile Glu Glu<br>295                       300                       305                       310 | 1146 |
| ccc aaa ctt ccc aag aac ttt ata gag gag tta aaa tta aca agt ggc<br>Pro Lys Leu Pro Lys Asn Phe Ile Glu Glu Leu Lys Leu Thr Ser Gly<br>                               315                       320                       325 | 1194 |
| aat aat aaa gga cta gtg gtg tca tgg tgt cca caa tta caa gtg ttg<br>Asn Asn Lys Gly Leu Val Val Ser Trp Cys Pro Gln Leu Gln Val Leu<br>                       330                       335                       340 | 1242 |
| gaa cat gaa tcg ata gga tgt ttt ctg acg cac tgt ggg tgg aat tcg<br>Glu His Glu Ser Ile Gly Cys Phe Leu Thr His Cys Gly Trp Asn Ser<br>                       345                       350                       355 | 1290 |
| act ctg gaa gca att agt ttg gga gtg cca atg gtg gca atg cca caa<br>Thr Leu Glu Ala Ile Ser Leu Gly Val Pro Met Val Ala Met Pro Gln<br>                       360                       365                       370 | 1338 |
| tgg aca gat caa cca act aat gca aaa ttt gtg aag gat gtt tgg gaa<br>Trp Thr Asp Gln Pro Thr Asn Ala Lys Phe Val Lys Asp Val Trp Glu<br>375                       380                       385                       390 | 1386 |
| ata ggt gtt aga gcc aaa caa gat gaa aaa ggg ata gtt aga aga gaa<br>Ile Gly Val Arg Ala Lys Gln Asp Glu Lys Gly Ile Val Arg Arg Glu<br>                       395                       400                       405 | 1434 |
| gtt att gaa gaa tgt ata aaa tta gtg atg gaa gaa gag aaa ggg aaa<br>Val Ile Glu Glu Cys Ile Lys Leu Val Met Glu Glu Glu Lys Gly Lys<br>                       410                       415                       420 | 1482 |
| tta att agg gaa aat gca aag aaa tgg aag gaa atg gct aga aat gtt<br>Leu Ile Arg Glu Asn Ala Lys Lys Trp Lys Glu Met Ala Arg Asn Val<br>                       425                       430                       435 | 1530 |
| gtg gat gaa gga gga agt tca gat aaa aat att gaa gaa ttt gtt tcc<br>Val Asp Glu Gly Gly Ser Ser Asp Lys Asn Ile Glu Glu Phe Val Ser<br>                       440                       445                       450 | 1578 |
| aag ttg gtt aaa tgt aag agt cat aaa aaa t aattaagtag ttgatttgta<br>Lys Leu Val Lys Cys Lys Ser His Lys Lys<br>455                       460 | 1629 |
| ttttgcaatt tcttttcta attaaagtag caaagtttga cttgaatctt cttttatttt | 1689 |
| ctcctctttg gttaaatgta agagtcataa aaaataactt atttgctaga tgattgaatg | 1749 |
| ctttatttgt catctcactt ttaatgaact tttgaatata attaa | 1794 |

<210> SEQ ID NO 2
<211> LENGTH: 464
<212> TYPE: PRT
<213> ORGANISM: Solanum tuberosum
<220> FEATURE:
<221> NAME/KEY: PEPTIDE
<222> LOCATION: (1)..(464)

<400> SEQUENCE: 2

Met Thr Thr His Gln Ala His Cys Leu Ile Leu Ser Tyr Pro Val Gln
1               5                   10                   15

-continued

```
Gly His Ile Asn Pro Met Leu Gln Phe Ser Lys Arg Leu Gln Ser Lys
             20                  25                  30
Arg Val Lys Ile Thr Ile Ala Leu Thr Lys Ser Phe Leu Lys Asn Met
         35                  40                  45
Lys Glu Leu Pro Thr Ser Met Ser Ile Glu Ala Ile Ser Asp Gly Tyr
 50                  55                  60
Asp Asp Gly Gly Arg Asp Gln Ala Gly Ser Phe Val Ala Tyr Val Thr
 65                  70                  75                  80
Arg Phe Lys Glu Val Gly Ser Asp Thr Leu Ser Gln Leu Ile Gln Lys
                 85                  90                  95
Leu Ala Asn Ser Gly Cys Pro Val Asn Cys Ile Val Tyr Asp Pro Phe
            100                 105                 110
Leu Pro Trp Ala Val Glu Val Ala Lys Asn Phe Gly Leu Ile Ser Ala
        115                 120                 125
Ala Phe Phe Thr Gln Asn Cys Ala Val Asp Asn Ile Tyr Tyr His Val
130                 135                 140
His Lys Gly Val Ile Lys Leu Pro Pro Thr Gln Asn Asn Glu Glu Ile
145                 150                 155                 160
Leu Ile Pro Gly Phe Ser Ser Pro Ile Glu Ala Ser Asp Ala Pro Thr
                165                 170                 175
Phe Val Ile Asp Pro Glu Ala Glu Arg Ile Leu Glu Met Leu Val Asn
            180                 185                 190
Gln Phe Ser Asn Leu Asp Lys Val Asp Trp Val Leu Ile Asn Ser Phe
        195                 200                 205
Tyr Glu Leu Glu Lys Glu Val Ile Asp Trp Met Ser Lys Met Tyr Pro
210                 215                 220
Ile Lys Thr Ile Gly Pro Thr Ile Pro Ser Met Tyr Leu Asp Lys Arg
225                 230                 235                 240
Leu His Asp Asp Lys Glu Tyr Gly Leu Ser Ile Phe Lys Pro Met Thr
                245                 250                 255
Asn Glu Cys Leu Asn Trp Leu Asn His Gln Pro Ile Ser Ser Val Val
            260                 265                 270
Tyr Val Ser Phe Gly Ser Leu Ala Lys Leu Glu Ala Glu Gln Met Glu
        275                 280                 285
Glu Leu Ala Cys Gly Leu Arg Asn Ser Asn Lys Asn Phe Leu Trp Val
290                 295                 300
Val Arg Ser Ile Glu Glu Pro Lys Leu Pro Lys Asn Phe Ile Glu Glu
305                 310                 315                 320
Leu Lys Leu Thr Ser Gly Asn Asn Lys Gly Leu Val Val Ser Trp Cys
                325                 330                 335
Pro Gln Leu Gln Val Leu Glu His Glu Ser Ile Gly Cys Phe Leu Thr
            340                 345                 350
His Cys Gly Trp Asn Ser Thr Leu Glu Ala Ile Ser Leu Gly Val Pro
        355                 360                 365
Met Val Ala Met Pro Gln Trp Thr Asp Gln Pro Thr Asn Ala Lys Phe
370                 375                 380
Val Lys Asp Val Trp Glu Ile Gly Val Arg Ala Lys Gln Asp Glu Lys
385                 390                 395                 400
Gly Ile Val Arg Arg Glu Val Ile Glu Cys Ile Lys Leu Val Met
                405                 410                 415
Glu Glu Glu Lys Gly Lys Leu Ile Arg Glu Asn Ala Lys Lys Trp Lys
            420                 425                 430
```

-continued

```
Glu Met Ala Arg Asn Val Val Asp Glu Gly Gly Ser Ser Asp Lys Asn
        435                 440                 445

Ile Glu Glu Phe Val Ser Lys Leu Val Lys Cys Lys Ser His Lys Lys
    450                 455                 460
```

PRODUCTION OF GENTISIC ACID 5-O-β-D XYLOPYRANOSIDE

Methods of producing gentisic acid 5-O-β-D xylopyranoside using polypeptides present in *Solanum tuberosum* that are capable of catalyzing the addition of UDP-xylose to gentisic acid to produce gentisic acid 5-O-β-D xylopyranoside and host cells, expression vectors, and transcription templates containing a heterologous regulatory element operably linked to a polynucleotide sequence derived from *Solanum tuberosum* that encodes such a polypeptide are described. Gentisic acid 5-O-β-D xylopyranoside produced by such methods and host cells can be applied to food products to enhance the saltiness perceived by an individual consuming such a food product.

BACKGROUND

Food technology that reduces the current utilization of dietary sodium in food production has the potential to reduce the incidence of health issues associated with high sodium intake and has important applications in the food and beverage industry. Thus, there is a demand for the food and beverage industry to develop food products having lower sodium levels without compromising on the salt taste that meets consumer expectations. In addition, natural flavoring agents are preferred over artificial flavoring agents by some consumers and can simplify food labeling. However, known salt substitutes may not be considered natural flavoring agents and are associated with low saltiness intensity and off-flavors. Accordingly, there is a need for natural compounds that enhance the perceived saltiness of a food product without adding sodium or off-flavors to the food product.

SUMMARY

According to one aspect of this disclosure, a polynucleotide includes a heterologous regulatory element operably linked to a polynucleotide sequence derived from *Solanum tuberosum* and encoding a xylosyltransferase. The transcription template is adapted for in vitro transcription in a cell-free system. The xylosyltransferase may be gentisate glycosyltransferase.

According to another aspect, an expression vector includes a heterologous regulatory element operably linked to a polynucleotide sequence derived from *Solanum tuberosum* and encoding a xylosyltransferase. The xylosyltransferase may be gentisate glycosyltransferase. This expression vector may be contained within a recombinant host cell capable of expressing the xylosyltransferase from the polynucleotide, the recombinant host cell selected from the group consisting of a bacterial cell, a fungal cell, an animal cell (e.g., a mammalian cell or an insect cell), or a plant cell.

According to another aspect, a method for producing gentisic acid 5-O-β-D xylopyranoside is disclosed. The method includes culturing a recombinant host cell. The recombinant host cell contains an expression vector that includes a polynucleotide comprising a heterologous regulatory element operably linked to a polynucleotide sequence derived from *Solanum tuberosum* and encoding a xylosyltransferase. The xylosyltransferase may be gentisate glycosyltransferase.

The recombinant host cell of this method is capable of expressing the xylosyltransferase from the polynucleotide and is selected from the group consisting of a bacterial cell, a fungal cell, an animal cell (e.g., a mammalian cell or an insect cell), or a plant cell. In one embodiment, the method further includes producing gentisic acid 5-O-β-D xylopyranoside by contacting the xylosyltransferase produced by the recombinant host cell with at least gentisic acid and UDP-xylose. In this embodiment, the contacting the expressed xylosyltransferase includes incubating the recombinant host cell with at least gentisic acid and UDP-xylose to produce gentisic acid 5-O-β-D xylopyranoside, and the method may further include extracting the gentisic acid 5-O-β-D xylopyranoside from the recombinant host cell.

According to another aspect, another recombinant host cell is disclosed. The recombinant host cell has a modified level of a xylosyltransferase relative to a wild-type cell of the same taxon. The recombinant host cell is capable of producing gentisic acid 5-O-β-D xylopyranoside when the xylosyltransferase is contacted with UDP-xylose and gentisic acid, and comprises a polynucleotide comprising a heterologous regulatory element operably linked to a polynucleotide sequence derived from *Solanum tuberosum* and encoding the xylosyltransferase. The xylosyltransferase may be gentisate glycosyltransferase. This recombinant host cell may be further capable of producing UDP-xylose and gentisic acid. In this embodiment, the recombinant host cell may have a modified level of at least one of UDP-xylose, gentisic acid, and gentisic acid 5-O-β-D xylopyranoside relative to the wild-type cell of the same taxon. The recombinant host cell in this embodiment may be incorporated into a multicellular structure, which may be plant tissue, such as plant tissue of a whole plant of the species *Solanum tuberosum*.

BRIEF DESCRIPTION OF SEQUENCES

SEQ ID NO: 1 is a non-naturally occurring DNA coding sequence encoding gentisate glycosyltransferase.

SEQ ID NO: 2 is an amino acid sequence of gentisate glycosyltransferase.

DESCRIPTION

Gentisic acid 5-O-β-D xylopyranoside, a compound endogenous to potatoes, has been shown to enhance the perception of saltiness when topically applied to food products such as potato chips without adding sodium or off-flavors to the food product. Moreover, due to its natural occurrence in potatoes, gentisic acid 5-O-β-D xylopyranoside in some cases may not need to be labeled when applied to potato-based products, thereby facilitating simple food labels desired by consumers. However, gentisic acid 5-O-β-D xylopyranoside is not readily available on a commercial basis and its purification from potatoes may not be economically feasible.

Therefore, methods of producing gentisic acid 5-O-β-D xylopyranoside using polypeptides present in the common potato, *Solanum tuberosum*, that are capable of catalyzing the addition of UDP-xylose and gentisic acid to produce gentisic acid 5-O-β-D xylopyranoside and host cells, expression vectors, and transcription templates containing a heterologous regulatory element operably linked to a polynucleotide sequence derived from *Solanum tuberosum* that encodes such a polypeptide are described.

Definitions

The term "nucleic acid" refers to deoxyribonucleotides or ribonucleotides and polymers thereof in either single- or double-stranded form, composed of monomers (nucleotides) containing a sugar, phosphate and a base that is either a purine or pyrimidine. Unless specifically limited, the term encompasses nucleic acids containing known analogs of natural nucleotides, conservatively modified variants thereof, complementary sequences, and degenerate codon substitutions that have similar binding properties as the reference nucleic acid and are metabolized in a manner similar to naturally occurring nucleotides.

The terms "nucleic acid," "nucleic acid molecule," "nucleic acid fragment," "nucleic acid sequence or segment," or "polynucleotide" are used interchangeably.

The term "vector" refers to any genetic element, such as a plasmid, phage, transposon, cosmid, chromosome, virus, virion, etc., which is capable of replication when associated with the proper control elements, such as a helper virus, and which can transfer gene sequences between cells. Thus, the term includes cloning and expression vehicles, as well as replication-defective viral vectors. Numerous types of vectors exist and are well known in the art.

The term "recombinant" when used with reference, e.g., to a cell, or nucleic acid, protein, or vector, indicates that the cell, nucleic acid, protein or vector, has been modified by the introduction of a heterologous nucleic acid or protein or the alteration of a native nucleic acid or protein, or that the cell is derived from a cell so modified. Thus, for example, recombinant cells express genes that are not found within the native (non-recombinant) form of the cell or express native genes that are otherwise abnormally expressed, under expressed or not expressed at all.

The term "heterologous" when used with reference to portions of a nucleic acid indicates that the nucleic acid comprises two or more subsequences that are not found in the same relationship to each other in nature. For instance, the nucleic acid is typically recombinantly produced, having two or more sequences from unrelated genes arranged to make a new functional nucleic acid, e.g., a promoter from one source and a coding region from another source. Similarly, a heterologous polypeptide indicates that the polypeptide comprises two or more subsequences that are not found in the same relationship to each other in nature (e.g., a fusion polypeptide).

The term "variant" of a molecule is a sequence that is substantially similar to the sequence of the reference molecule. For nucleotide sequences, variants include those sequences that, because of the degeneracy of the genetic code, encode the identical amino acid sequence of the reference protein. Naturally occurring allelic variants such as these can be identified with the use of molecular biology techniques, as, for example, with polymerase chain reaction (PCR) and hybridization techniques. Variant nucleotide sequences also include synthetically derived nucleotide sequences, such as those generated, for example, by using site-directed mutagenesis, which encode the reference protein, as well as those that encode a polypeptide having amino acid substitutions. Generally, nucleotide sequence variants of the invention will have at least about 40%, 50%, 60%, 70%, 80%, 90%, 95%, 96%, 97%, 98%, to 99% sequence identity to the reference (endogenous) nucleotide sequence.

The term "conservatively modified variations" of a particular nucleic acid sequence refers to those nucleic acid sequences that encode identical or essentially identical amino acid sequences. Because of the degeneracy of the genetic code, a large number of functionally identical nucleic acids encode any given polypeptide. For instance, the codons CGT, CGC, CGA, CGG, AGA and AGG all encode the amino acid arginine. Thus, at every position where an arginine is specified by a codon, the codon can be altered to any of the corresponding codons described without altering the encoded protein. Such nucleic acid variations are "silent variations," which are one species of "conservatively modified variations." Every nucleic acid sequence described herein that encodes a polypeptide also describes every possible silent variation, except where otherwise noted. One of skill in the art will recognize that most codons in a nucleic acid can be modified to yield a functionally identical molecule by standard techniques. Accordingly, each "silent variation" of a nucleic acid that encodes a polypeptide is implicit in each described sequence.

The terms "substantially identical" or "substantial identity," in the context of two or more nucleic acids or polypeptide sequences, refer to two or more sequences or subsequences that are the same or have a specified percentage of amino acid residues or nucleotides that are the same (i.e., at least about 60%, preferably 65%, 70%, 75%, preferably 80%, 85%, 90%, 91%, 92%, 93%, 94%, 95%, 96%, 97%, 98% or 99% identity over a specified region), when compared and aligned for maximum correspondence over a comparison window, or designated region as measured using one of the following sequence comparison algorithms or by manual alignment and visual inspection. This definition, when the context indicates, also refers analogously to the complement of a sequence, such as an RNA nucleotide complementary to a DNA nucleotide. Preferably, the substantial identity exists over a region that is at least about 6-7 amino acids or 25 nucleotides in length.

An example of an algorithm that is suitable for determining percent sequence identity and sequence similarity is the BLAST algorithm, which is described in Altschul et al., 1977, Nuc. Acids Res. 25:3389-3402. BLAST is used, with the parameters described herein, to determine percent sequence identity for the nucleic acids and proteins of the invention. Software for performing BLAST analysis is publicly available through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) or 10, M=5, N=−4 and a comparison of both strands. For amino acid sequences, the BLASTP program uses as defaults a wordlength of 3, and expectation (E) of 10, and the BLOSUM62 scoring matrix (see Henikoff & Henikoff, Proc. Natl. Acad. Sci. USA, 89:10915 (1989)) alignments (B) of 50, expectation (E) of 10, M=5, N=−4, and a comparison of both strands. The TBLASTN program (for translated nucleotide sequences compared to protein) uses as defaults a wordlength (W) of X, an expectation (E) or X, M=X, N=X and a comparison of both strands.

The BLAST algorithm also performs a statistical analysis of the similarity between two sequences (see, e.g., Karlin & Altschul, Proc. Nat'l. Acad. Sci. USA, 90:5873-5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01, and most preferably less than about 0.001.

The practice of the disclosure will employ, unless indicated specifically to the contrary, conventional methods of chemistry, biochemistry, organic chemistry, molecular biology, microbiology, recombinant DNA techniques, genetics, immunology, and cell biology that are within the skill of the art, many of which are described below for the purpose of illustration. Such techniques are explained fully in the literature. See, e.g., Sambrook, et al., *Molecular Cloning: A Laboratory Manual* (3rd Edition, 2001); Sambrook, et al., *Molecular Cloning: A Laboratory Manual* (2nd Edition, 1989); Maniatis et al., *Molecular Cloning: A Laboratory Manual* (1982); Ausubel et al., *Current Protocols in Molecular Biology* (John Wiley and Sons, updated July 2008); *Short Protocols in Molecular Biology: A Compendium of Methods from Current Protocols in Molecular Biology*, Greene Pub. Associates and Wiley-Interscience; Glover, DNA Cloning: *A Practical Approach*, vol. I & II (IRL Press, Oxford, 1985); Anand, *Techniques for the Analysis of Complex Genomes*, (Academic Press, New York, 1992); *Transcription and Translation* (B. Hames & S. Higgins, Eds., 1984); Perbal, *A Practical Guide to Molecular Cloning* (1984); Harlow and Lane, *Antibodies*, (Cold Spring Harbor Laboratory Press, Cold Spring Harbor, N.Y., 1998) *Current Protocols in Immunology* Q. E. Coligan, A. M. Kruisbeek, D. H. Margulies, E. M. Shevach and W. Strober, eds., 1991); *Annual Review of Immunology*; as well as monographs in journals such as *Advances in Immunology*.

Polypeptides

Polypeptides of the present disclosure glycosylate gentisic acid, by transferring a xylose from UDP-xylose to the gentisic acid, to produce gentisic acid 5-O-β-D xylopyranoside. In some embodiments, the polypeptides may include amino acid substitutions, deletions, truncations, and insertions and still function to glycosylate gentisic acid to produce gentisic acid 5-O-β-D xylopyranoside. Methods for such manipulations are generally known in the art. For example, amino acid sequence variants of a reference polypeptide may be prepared by mutations in the DNA. Methods for mutagenesis and nucleotide sequence alterations are well known in the art. See, for example, Kunkel (1985, Proc. Natl. Acad. Sci. USA. 82: 488-492), Kunkel et al., (1987, Methods in Enzymol, 154: 367-382), U.S. Pat. No. 4,873, 192, Watson, J. D. et al., (Molecular Biology of the Gene, Fourth Edition, Benjamin/Cummings, Menlo Park, Calif., 1987) and the references cited therein. Guidance as to appropriate amino acid substitutions that do not affect biological activity of the protein of interest may be found in the model of Dayhoff et al., (1978) Atlas of Protein Sequence and Structure (Natl. Biomed. Res. Found., Washington, D.C.).

Recombinant Expression Vectors and Host Cells

In some embodiments, vectors, for example, recombinant expression vectors, containing a nucleic acid encoding a polypeptide to produce gentisate glycosyltransferase are disclosed. The term "vector" is used herein to refer to a nucleic acid molecule capable transferring or transporting another nucleic acid molecule. The transferred nucleic acid is generally linked to, e.g., inserted into, the vector nucleic acid molecule. A vector may include sequences that direct autonomous replication in a cell, or may include sequences sufficient to allow integration into host cell DNA. Examples of vectors are plasmids (e.g., DNA plasmids or RNA plasmids), autonomously replicating sequences, and transposable elements. Additional exemplary vectors include, without limitation, plasmids, phagemids, cosmids, artificial chromosomes such as yeast artificial chromosome (YAC), bacterial artificial chromosome (BAC), or PI-derived artificial chromosome (PAC), bacteriophages such as lambda phage or M13 phage, and animal viruses. Examples of categories of animal viruses useful as vectors include, without limitation, retrovirus (including lentivirus), adenovirus, adeno-associated virus, herpesvirus (e.g., herpes simplex virus), poxvirus, baculovirus, papillomavirus, and papovavirus (e.g., SV40). Examples of expression vectors are pCIneo vectors (Promega) for expression in mammalian cells; pLenti4N5—DEST™, pLenti6N5—DEST™, and pLenti6.2N5—GW/lacZ (Invitrogen) for lentivirus-mediated gene transfer and expression in mammalian cells. In certain embodiments, useful viral vectors include, e.g., replication defective retroviruses and lentiviruses. Exemplary plant expression vectors include, without limitation, pCambia2301 Plant Expression Vector.

The recombinant expression vectors can include a nucleic acid encoding a polypeptide to produce gentisate glycosyltransferase described herein in a form suitable for expression of the nucleic acid in a host cell, which means that the recombinant expression vectors include one or more regulatory sequences, selected on the basis of the host cells to be used for expression, which is operatively linked to the nucleic acid sequence to be expressed. The "control elements" or "regulatory sequences" present in an expression vector are those non-translated regions of the vector-origin of replication, selection cassettes, promoters, enhancers, translation initiation signals (Shine Dalgarno sequence or Kozak sequence), introns, a polyadenylation sequence, 5' and 3' untranslated regions—which interact with host cellular proteins to carry out transcription and translation. Such elements may vary in their strength and specificity. Depending on the vector system and host utilized, any number of suitable transcription and translation elements, including ubiquitous promoters and inducible promoters maybe used.

The term "promoter" as used herein refers to a recognition site of a polynucleotide (DNA or RNA) to which an RNA polymerase binds. An RNA polymerase initiates and transcribes polynucleotides operably linked to the promoter. In particular embodiments, promoters operative in mammalian cells comprise an AT-rich region located approximately 25 to 30 bases upstream from the site where transcription is initiated and/or another sequence found 1,000-5,000 bases upstream from the start of transcription, a CNCAAT region where N may be any nucleotide.

The term "enhancer" refers to a segment of DNA which contains sequences capable of providing enhanced transcription and in some instances may function independent of their orientation relative to another control sequence. An enhancer may function cooperatively or additively with promoters and/or other enhancer elements. The term "promoter/enhancer" refers to a segment of DNA which contains sequences capable of providing both promoter and enhancer functions.

The term "operably linked", refers to a juxtaposition wherein the components described are in a relationship permitting them to function in their intended manner. In one embodiment, the term refers to a functional linkage between a nucleic acid expression control sequence (such as a promoter, and/or enhancer) and a second polynucleotide sequence, e.g., a polynucleotide—of interest, wherein the expression control sequence directs transcription of the nucleic acid corresponding to the second sequence.

As used herein, the term "constitutive expression control sequence" refers to a promoter, enhancer, or promoter/enhancer that continually or continuously allows for transcription of an operably linked sequence. A constitutive expression control sequence may be a "ubiquitous" promoter, enhancer, or promoter/enhancer that allows expression in a wide variety of cell and tissue types or a "cell specific," "cell type specific," "cell lineage specific," or "tissue specific" promoter, enhancer, or promoter/enhancer that allows expression in a restricted variety of cell and tissue types, respectively.

Illustrative ubiquitous expression control sequences suitable for use in particular embodiments of the disclosure in which a recombinant host cell is a plant cell include, but are not limited to, those from nopaline synthase (nos), octopine synthase (ocs) and cauliflower mosaic virus (CaMV) genes. One type of efficient plant promoter that may be used is a high level plant promoter. Such promoters, in operable linkage with an expression vector of the subject technology should be capable of promoting the expression of the vector. High level plant promoters that may be used in the subject technology include the promoter of the small subunit (ss) of the ribulose-1,5-bisphosphate carboxylase for example from soybean (Berry-Lowe et al., J. Molecular and App. Gen., 1:483 498 (1982), the entirety of which is hereby incorporated herein to the extent it is consistent herewith), and the promoter of the chlorophyll a/b binding protein. These two promoters are known to be light-induced in plant cells (see, for example, Genetic Engineering of Plants, an Agricultural Perspective, A. Cashmore, Plenum, N.Y. (1983), pages 29 38; Coruzzi, G. et al., The Journal of Biological Chemistry, 258:1399 (1983), and Dunsmuir, P. et al., Journal of Molecular and Applied Genetics, 2:285 (1983), each of which is hereby incorporated herein by reference to the extent they are consistent herewith).

Illustrative ubiquitous expression control sequences suitable for use in particular embodiments of the disclosure a recombinant host cell is a microbial host cell include, but are not limited to, CYC1, HIS3, GAL1, GAL10, ADH1, PGK, PHO5, GAPDH, ADC1, TRP1, URA3, LEU2, ENO, TPI (useful for expression in *Saccharomyces*); AOX1 (useful for expression in *Pichia*); and lac, trp, $IP_L$, $IP_R$, T7, tac, and trc (useful for expression in *Escherichia coli*).

As used herein, "conditional expression" may refer to any type of conditional expression including, but not limited to, inducible expression; repressible expression; expression in cells or tissues having a particular physiological, biological, or disease state, etc. This definition is not intended to exclude cell type or tissue specific expression. Certain embodiments described herein provide conditional expression of a polynucleotide-of-interest, e.g., expression is controlled by subjecting a cell, tissue, organism, etc., to a treatment or condition that causes the polynucleotide to be expressed or that causes an increase or decrease in expression of the polynucleotide encoded by the polynucleotide-of-interest.

Illustrative examples of inducible promoters/systems include, but are not limited to, steroid-inducible promoters such as promoters for genes encoding glucocorticoid or estrogen receptors (inducible by treatment with the corresponding hormone), metallothionine promoter (inducible by treatment with various heavy metals), MX-1 promoter (inducible by interferon), lac operon promoter (inducible by isopropyl β-d-1-thiogalactopyranoside (IPTG)), the "Gene-Switch" mifepristone-regulatable system (Sirin et al., 2003, Gene, 323:67), the cumate-inducible gene switch (WO 2002/088346), tetracycline-dependent regulatory systems, etc.

Conditional expression may also be achieved by using a site specific DNA recombinase. According to certain embodiments of the disclosure the vector comprises at least one (typically two) site(s) for recombination mediated by a site specific recombinase. As used herein, the terms "recombinase" or "site specific recombinase" include excisive or integrative proteins, enzymes, cofactors or associated proteins that are involved in recombination reactions involving one or more recombination sites (e.g., two, three, four, five, seven, ten, twelve, fifteen, twenty, thirty, fifty, etc.), which may be wild-type proteins (see Landy, Current Opinion in Biotechnology 3:699-707 (1993)), or mutants, derivatives (e.g., fusion proteins containing the recombination protein sequences or fragments thereof), fragments, and variants thereof. Illustrative examples of recombinases suitable for use in particular embodiments of the present disclosure include, but are not limited to: Cre, Int, IHF, Xis, Flp, Fis, Hin, Gin, φC31, Cin, Tn3 resolvase, TndX, XerC, XerD, TnpX, Hjc, Gin, SpCCEI, and ParA.

Expression of proteins in prokaryotes is most often carried out in *E. coli* with vectors containing constitutive or inducible promoters directing the expression of either fusion or non-fusion proteins. Fusion vectors add a number of amino acids to a protein encoded therein, usually to the amino terminus of the recombinant protein. Such fusion vectors typically serve three purposes: 1) to increase expression of recombinant protein; 2) to increase the solubility and/or stability of the recombinant protein; and 3) to aid in the purification of the recombinant protein by acting as a ligand in affinity purification. Often, in fusion expression vectors, a proteolytic cleavage site is introduced at the junction of the fusion moiety and the recombinant protein to enable separation of the recombinant protein from the fusion moiety subsequent to purification of the fusion protein. Such enzymes, and their cognate recognition sequences, include Factor Xa, thrombin and enterokinase. Typical fusion expression vectors include pGEX (Pharmacia Biotech Inc; Smith, D. B. and Johnson, K. S. (1988) Gene 67:31-40), pMAL (New England Biolabs, Beverly, Mass.) and pRIT5 (Pharmacia, Piscataway, N.J.) which fuse glutathione S-transferase (GST), maltose E binding protein, or protein A, respectively, to the target recombinant protein.

Examples of suitable inducible non-fusion *E. coli* expression vectors include pTrc (Amann et al., (1988) Gene 69:301-315) and pET 11d (Studier et al., Gene Expression Technology Methods in Enzymology 185, Academic Press, San Diego, Calif. (1990) 60-89). Target gene expression from the pTrc vector relies on host RNA polymerase transcription from a hybrid trp-lac fusion promoter. Target gene expression from the pET 11d vector relies on transcription from a T7 gn10-lac fusion promoter mediated by a coexpressed viral RNA polymerase (T7 gn1). This viral polymerase is supplied by host strains BL21(DE3) or HMS174 (DE3) from a resident prophage harboring a T7 gn1 gene under the transcriptional control of the lacUV 5 promoter.

One strategy to maximize recombinant protein expression in *E. coli* is to express the protein in a host bacteria with an impaired capacity to proteolytically cleave the recombinant protein (Gottesman, S., Gene Expression Technology: Methods in Enzymology 185, Academic Press, San Diego, Calif. (1990) 119-128). In such strategies, the bacteria may be food-grade microbes; e.g., food-grade microbes with FDA generally-recognized-as-safe (GRAS) status. Another strategy is to alter the nucleic acid sequence of the nucleic acid to be inserted into an expression vector so that the individual codons for each amino acid are those preferentially utilized in *E. coli* (Wada et al., (1992) Nucleic Acids Res. 20:2111-2118). Such alteration of nucleic acid sequences of the invention can be carried out by standard DNA synthesis techniques.

In another embodiment, the expression vector is a yeast expression vector. Examples of vectors for expression in yeast *S. cerevisiae* include pYepSec1 (Baldari, et al., (1987) EMBO J. 6:229-234), pMFa (Kurjan and Herskowitz, (1982) Cell 30:933-943), pJRY88 (Schultz et al., (1987) Gene 54:113-123), pYES2 (Invitrogen Corporation, San Diego, Calif.), and picZ (InVitrogen Corp, San Diego, Calif.).

In some embodiments, host cells into which a nucleic acid molecule encoding a polypeptide to produce a xylosyltransferase, such as gentisate glycosyltransferase, is introduced may be used. The terms "host cell" and "recombinant host cell" are used interchangeably herein. It is understood that such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

A host cell can be any prokaryotic or eukaryotic cell. For example, a polypeptide to produce gentisate glycosyltransferase or fusion protein can be expressed in plant cells, bacterial cells such as *E. coli*, insect cells, yeast or mammalian cells (such as hematopoietic cells, leukocytes, K562 cells, 293T cells, human umbilical vein endothelial cells (HUVEC), human microvascular endothelial cells (HMVEC), Chinese hamster ovary cells (CHO) or COS cells). Other suitable host cells are known to those skilled in the art. A host cell, such as a prokaryotic or eukaryotic host cell in culture, may be used to produce (i.e., express) a polypeptide to produce a xylosyltransferase.

The conversion of gentisic acid and UDP-xylose to gentisic acid 5-O-β-D xylopyranoside will now be described. Gentisic acid 5-O-β-D xylopyranoside has been shown to enhance the perception of saltiness when topically applied to food products without adding sodium or off-flavors to the food product and thus is commercially valuable to the development of food products having lower sodium levels without compromising on the salt taste that meets consumer expectations.

The present disclosure is directed to non-naturally occurring polynucleotides that encode gentisate glycosyltransferase, a xylosyltransferase enzyme. The present disclosure is further directed to polynucleotides that include a heterologous regulatory element operably linked to a polynucleotide sequence encoding gentisate glycosyltransferase. Gentisate glycosyltransferase has been found to readily convert gentisic acid and UDP-xylose to gentisic acid 5-O-β-D xylopyranoside and may be used, for example, in bioconversion and/or fermentation strategies and bioengineering strategies for the production of gentisic acid 5-O-β-D xylopyranoside. The polynucleotides of the present disclosure and applications thereof are discussed in further detail below.

Polynucleotides

A xylosyltransferase enzyme; specifically, gentisate glycosyltransferase, has been identified in *Solanum tuberosum*. The gene sequence for gentisate glycosyltransferase has been isolated from this species, from which corresponding cDNA and an amino acid sequence have been produced. The DNA coding sequence encoding gentisate glycosyltransferase is shown in SEQ ID NO: 1 and the amino acid sequence of gentisate glycosyltransferase is shown in SEQ ID NO: 2. Polynucleotides comprising SEQ ID NO: 1 may be produced using known commonly-known synthesis and genetic engineering techniques and expressed as a recombinant protein in a host organism or in an in vitro cell-free system.

In some examples, the polynucleotides and amino acid sequences described herein may have greater than 80% identity to one of SEQ ID NO: 1 and SEQ ID NO: 2, such as 85%, 90%, 95%, 100%, or approximations thereof. For the sake of clarity, an embodiment described as including or using the nucleotide sequence of SEQ ID NO: 1 should be understood to respectively include a polynucleotide having at least 80% identity to the nucleotide sequence of SEQ ID NO: 1. Similarly, embodiments described as using or including the amino acid sequence of SEQ ID NO: 2 should be understood to respectively include a polynucleotide comprising a heterologous regulatory element operably linked to a polynucleotide sequence encoding a polypeptide comprising an amino acid sequence having at least 80% identity to the amino acid sequence of SEQ ID NO: 2.

Expression Vectors and Recombinant Hosts Containing the Polynucleotides

The DNA coding sequence of SEQ ID NO: 1 or a polynucleotide that includes a heterologous regulatory element operably linked to a polynucleotide sequence encoding a polypeptide comprising the amino acid sequence of SEQ ID NO: 2 may be inserted into an expression vector using standard techniques.

Such expression vectors may be tailored for expression of gentisate glycosyltransferase in a particular type of recombinant host cell or multicellular organism that includes one or more such recombinant host cells by incorporation of suitable regulatory sequences such as enhancers, promoters, 5' and/or 3' UTRs. The recombinant host cell may be selected from a bacterial cell, a fungal cell, an animal cell (e.g., a mammalian cell or an insect cell), or a plant cell. Example recombinant host cells may include strains of *E. coli*, *Saccharomyces* species, algal cells, and the like. Further example host cells may be selected from plant cells from plants such as cereal crops such as rice, rye, sorghum, millet, wheat, maize, and barley. The plant may be a non-cereal monocot such as asparagus, banana, or onion. The plant also may be a dicot such as potato (*Solanum tuberosum*), soybean, cotton, sunflower, pea, geranium, spinach, or tobacco. A multicellular organism of such embodiments may be a suitable plant; e.g., any suitable cereal plant, non-cereal monocot, or dicot.

The expression vectors containing the DNA coding sequence of SEQ ID NO: 1 or a polynucleotide that includes a heterologous regulatory element operably linked to a polynucleotide sequence encoding a polypeptide comprising the amino acid sequence of SEQ ID NO: 2 may be introduced into the recombinant host cell using known suitable techniques for introducing exogenous polynucleotides into the type of cell.

In other examples, the DNA coding sequence of SEQ ID NO: 1 or a polynucleotide that includes a heterologous regulatory element operably linked to a polynucleotide sequence encoding a polypeptide comprising the amino acid sequence of SEQ ID NO: 2 may be used in a bioengineering strategy for expression of gentisate glycosyltransferase in multicellular plants.

Methods of Producing Gentisate Glycosyltransferase Via the Polynucleotides

In some embodiments, gentisic acid 5-O-β-D xylopyranoside may be produced in vivo within a recombinant host cell containing an expression vector as described above. The recombinant host cell may be cultured under conditions in which the cell expresses recombinant gentisate glycosyltransferase. Under the culture conditions, the recombinant host cell is incubated with a substrate that contains UDP-xylose and gentisic acid. The gentisate glycosyltransferase expressed by the cell glycosylates gentisic acid, by transferring a xylose from UDP-xylose to the gentisic acid, to produce gentisic acid 5-O-β-D xylopyranoside. The gentisic acid 5-O-β-D xylopyranoside may be extracted from the recombinant host cell and processed and/or used as desired, for example, applied to a food product to enhance the saltiness perceived by an individual consuming the food product. For example, the gentisic acid 5-O-β-D xylopyranoside may be mixed with a flavor or seasoning blend, or added to a carrier before application to a food product.

In other embodiments, the recombinant host cell containing an expression vector as described above may be cultured under conditions in which the cell expresses recombinant gentisate glycosyltransferase. The gentisate glycosyltransferase may be extracted from the host cell and combined with UDP-xylose and gentisic acid to produce gentisic acid 5-O-β-D xylopyranoside. The gentisic acid 5-O-β-D xylopyranoside obtained in this manner also may be processed and/or used as desired, for example, applied to a food product to enhance the saltiness perceived by an individual consuming the food product. For example, the gentisic acid 5-O-β-D xylopyranoside may be mixed with a flavor or seasoning blend, or added to a carrier before application to a food product.

In other embodiments, the recombinant host cell containing an expression vector as described above may be cultured under conditions in which the cell expresses recombinant gentisate glycosyltransferase at a modified level relative to a wild-type cell of the same taxon. In such other embodiments, the recombinant host cell is capable of producing gentisic acid 5-O-β-D xylopyranoside when the recombinant gentisate glycosyltransferase is contacted with UDP-xylose and gentisic acid. The recombinant host cell may be further capable of producing the UDP-xylose and gentisic acid. In this instance, the recombinant host cell may produce the UDP-xylose and/or the gentisic acid at a modified level relative to the wild-type cell of the same taxon. The gentisic acid 5-O-β-D xylopyranoside obtained from the recombinant host cell of this embodiment may be processed and/or used as desired, for example, applied to a food product to enhance the saltiness perceived by an individual consuming the food product. In some such embodiments, the gentisic acid 5-O-β-D xylopyranoside may be mixed with a flavor or seasoning blend, or added to a carrier before application to a food product. Optionally, the recombinant host cell of this embodiment may be incorporated into a multicellular structure, such plant tissue; e.g., tissue of a whole plant of the species *Solanum tuberosum* or another suitable species.

In still other embodiments, a transcription template as described above (e.g., a linearized plasmid, PCR product, or cDNA converted to double-stranded template) may be used in an in vitro reaction to produce recombinant gentisate glycosyltransferase. The gentisate glycosyltransferase produced in this manner may be combined with UDP-xylose and gentisic acid to produce gentisic acid 5-O-β-D xylopyranoside. The gentisic acid 5-O-β-D xylopyranoside obtained in this manner also may be processed and/or used as desired, for example, applied to a food product to enhance the saltiness perceived by an individual consuming the food product. For example, the gentisic acid 5-O-β-D xylopyranoside may be mixed with a flavor or seasoning blend, or added to a carrier before application to a food product.

In still other embodiments, gentisic acid 5-O-β-D xylopyranoside may be produced in vivo within a multicellular organism (e.g., a host plant) produced via a bioengineering strategy to bear the DNA coding sequence of SEQ ID NO: 1 or a polynucleotide that includes a heterologous regulatory element operably linked to a polynucleotide sequence encoding a polypeptide comprising the amino acid sequences of SEQ ID NO: 2. The host plant may be grown under conditions in which it expresses recombinant gentisate glycosyltransferase. Under the growth conditions, the host plant is provided with a substrate that contains UDP-xylose and gentisic acid. The gentisate glycosyltransferase expressed by the host plant glycosylates gentisic, by transferring a xylose from UDP-xylose to the gentisic acid, to produce gentisic acid 5-O-β-D xylopyranoside. The gentisic acid 5-O-β-D xylopyranoside may be extracted from the host plant and processed and/or used as desired, for example, applied to a food product to enhance the saltiness perceived by an individual consuming the food product. For example, the gentisic acid 5-O-β-D xylopyranoside may be mixed with a flavor or seasoning blend, or added to a carrier before application to a food product.

In still other embodiments, a multicellular organism (e.g., a host plant) produced via a bioengineering strategy as described above may be grown under conditions in which the cell expresses recombinant gentisate glycosyltransferase. The gentisate glycosyltransferase may be extracted from the host plant and combined with UDP-xylose and gentisic acid to produce gentisic acid 5-O-β-D xylopyranoside. The gentisic acid 5-O-β-D xylopyranoside obtained in this manner also may be processed and/or used as desired, for example, applied to a food product to enhance the saltiness perceived by an individual consuming the food product. For example, the gentisic acid 5-O-β-D xylopyranoside may be mixed with a flavor or seasoning blend, or added to a carrier before application to a food product.

In some embodiments, inbred *Solanum tuberosum* plant lines may be identified that include a modified level of gentisate glycosyltransferase relative to a conventional *Solanum tuberosum*, plant material or seed, wherein the inbred *Solanum tuberosum* plant line includes one or more desired mutant alleles of a gene encoding the gentisate glycosyltransferase. In some embodiments, the inbred *Solanum tuberosum* plant lines may have a trait of accumulating a desired gentisate glycosyltransferase chemical profile. In some embodiments, *Solanum tuberosum* plant lines having one or more genetic modifications to introduce a gene encoding the gentisate glycosyltransferase may be screened to determine plant lines having the desired amount of expression of the gentisate glycosyltransferase relative to a wild type *Solanum tuberosum* plant line. The amount of expression may be increased or decreased relative to the wild type plant line. In some embodiments, the amount of expression may be increased relative to the wild type plant line.

While the concepts of the present disclosure are susceptible to various modifications and alternative forms, it should be understood, however, that there is no intent to limit the concepts of the present disclosure to the particular disclosed forms; the intention is to cover all modifications, equivalents, and alternatives falling within the spirit and scope of the invention as defined by the claims.

The invention claimed is:

1. A transcription template comprising a polynucleotide that comprises a heterologous regulatory element operably linked to a polynucleotide sequence SEQ ID NO: 1 from *Solanum tuberosum* encoding a xylosyltransferase comprising an amino acid sequence of SEO ID NO: 2, wherein the transcription template is adapted for in vitro transcription in a cell-free system.

2. An expression vector comprising a polynucleotide comprising a heterologous regulatory element operably linked to a polynucleotide sequence SEQ ID NO: 1 from *Solanum tuberosum* encoding a xylosyltransferase having an amino acid sequence SEO ID NO: 2, the expression vector contained within a recombinant host cell capable of expressing the xylosyltransferase from the polynucleotide and wherein the recombinant host cell is a bacterial cell, a fungal cell, an animal cell, or a plant cell.

3. A method for producing gentisic acid 5-O-l3-D xylopyranoside Comprising introducing the expression vector of claim 2 into a recombinant host cell and culturing the recombinant host cell under conditions in which the recombinant host cell expresses the xylosyltransferase from the polynucleotide.

4. The method of claim 3, further comprising contacting the expressed xylosyltransferase with gentisic acid and UDP-xylose.

5. The method of claim 4, wherein the contacting the expressed xylosyltransferase includes incubating the recombinant host cell with at least gentisic acid and UDP-xylose to produce gentisic acid 5-O-β-D xylopyranoside, the method further comprising extracting the gentisic acid 5-O-β-D xylopyranoside from the recombinant host cell.

6. The method of claim 3, 4, or 5, wherein the recombinant host cell is a plant cell.

7. A recombinant host cell comprising a modified level of a xylosyltransferase relative to the corresponding wild-type cell, wherein the recombinant host cell is capable of producing gentisic acid 5-O-l3-D xylopyranoside when the xylosyltransferase is contacted with UDP-xylose and gentisic acid, and wherein the recombinant host cell comprises a polynucleotide comprising a heterologous regulatory element operably linked to a polynucleotide sequence SEQ ID NO: 1 from *Solanum tuberosum* encoding the xylosyltransferase, wherein the xylosyltransferase comprises an amino acid sequence SEQ ID NO: 2.

8. The recombinant host cell of claim 7, wherein the recombinant host cell is a plant cell.

9. The recombinant host cell of claim 8, wherein the recombinant host cell comprises a modified level of at least one of UDP-xylose and gentisic acid relative to the wild-type cell.

10. The recombinant host cell of claim 8, wherein the recombinant host cell comprises a modified level of gentisic acid 5-O-l3-D xylopyranoside relative to the wildtype cell.

11. A multicellular structure comprising one or more cells according to claim 7, 8, 9, or 10.

12. The multicellular structure of claim 11, wherein the multicellular structure comprises plant tissue.

13. The multicellular structure of claim 12, wherein the plant tissue comprises tissue of a plant of the species *Solanum tuberosum*.

\* \* \* \* \*